United States Patent
Brown et al.

(10) Patent No.: US 7,045,625 B2
(45) Date of Patent: May 16, 2006

(54) ASYMMETRIC PROCESS FOR THE PREPARATION OF DIARYLETHYLPIPERAZINES DERIVATIVES AND NOVEL ASYMMETRIC DIARYLMETHYLAMINES AS INTERMEDIATES

(75) Inventors: William Brown, St. Laurent (CA); Niklas Plobeck, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 350 days.

(21) Appl. No.: 10/468,989

(22) PCT Filed: Mar. 5, 2002

(86) PCT No.: PCT/SE02/00376

§ 371 (c)(1),
(2), (4) Date: Aug. 25, 2003

(87) PCT Pub. No.: WO02/070492

PCT Pub. Date: Sep. 12, 2002

(65) Prior Publication Data

US 2004/0077861 A1    Apr. 22, 2004

(30) Foreign Application Priority Data

Mar. 7, 2001    (SE) .................................... 0100764

(51) Int. Cl.
| | |
|---|---|
| *C07D 401/00* | (2006.01) |
| *C07D 403/00* | (2006.01) |
| *C07D 405/00* | (2006.01) |
| *C07D 409/00* | (2006.01) |
| *C07D 413/00* | (2006.01) |

(52) U.S. Cl. ...................... 544/360; 544/363; 544/364; 544/366; 544/368; 544/370; 544/396

(58) Field of Classification Search ................ 544/360, 544/363, 364, 366, 368, 370, 396
See application file for complete search history.

(56) References Cited

FOREIGN PATENT DOCUMENTS

| WO | WO 93/15062 | * | 8/1993 |
|---|---|---|---|
| WO | WO 95/04051 | * | 2/1995 |
| WO | WO 9723466 | | 7/1997 |
| WO | WO 0145637 | | 6/2001 |
| WO | WO 0174805 | | 10/2001 |

OTHER PUBLICATIONS

Delorme et al, "Asymmetric Synthesis of Diarylmethylamines: Preparation of Selective Opioid delta-Receptor Ligands" Tetrahedron: Asymmetry, vol. 9, pp. 3963-3966 (1998).*

* cited by examiner

Primary Examiner—James O. Wilson
Assistant Examiner—Zachary C. Tucker
(74) Attorney, Agent, or Firm—Jianzhong Shen

(57) ABSTRACT

An asymmetric synthesis of diarylmethylpiperazines is described. The synthetic route enables preparation of a variety of enatiomerically pure amines with different N-alkyl groups. The invention includes an asymmetric addition of organometallic compounds to chiral sulfinimine to give adducts in predominantly one diastereomer can subsequently be transferred into pure enantiomers of by cleavage of the chiral auxilliary which is followed by synthesis of the piperazine ring by alkylation procedures.

6 Claims, No Drawings

ASYMMETRIC PROCESS FOR THE PREPARATION OF DIARYLETHYLPIPERAZINES DERIVATIVES AND NOVEL ASYMMETRIC DIARYLMETHYLAMINES AS INTERMEDIATES

CROSS-REFERENCE TO RELATED APPLICATIONS

This application is a US National Stage of International Application No. PCT/SE02/00376 which was filed on Mar. 5, 2002. The International Application claims priority under 35 U.S.C. 119(a) to Swedish Application No. 0100764-0 filed Mar. 7, 2001.

FIELD OF THE INVENTION

The present invention relates to a novel asymmetric process for the preparation of diarylmethylpiperazines derivatives and to novel asymmetric diarylmethylamines as intermediates.

BACKGROUND OF THE INVENTION AND PRIOR ART

Diarylmethylamines are an important class of amines present in many compounds with biological activity, for example diarylmethylpiperazines, and constitutes key intermediates in the synthesis of these compounds. Most preparations of enantiomerically pure diarylmethyl-amines and -piperazines rely on resolution of diastereomers by crystallization were half of the material is discarded.

There are few reports on asymmetric synthesis of diarylmethylpiperazines. The present invention describes a simple and practical process for asymmetric synthesis of diarylmethylpiperazines in high yield and enantiomeric purity with asymmetric diarylmethylamines as intermediates. The process relies on diastereoselective addition of organometallic compounds to chiral sulfinimines.

Diarylmethylpiperazines derivatives are known from inter alia WO 93/15062, WO 95/04051, and WO 97/23466 to have analgesic effect. The diarylmethylpiperazines derivatives are prepared starting from an N-unsubstituted piperazine derivative which is thereafter alkylated to give the desired diarylmethylpiperazines.

DESCRIPTION OF THE INVENTION

An asymmetric synthesis of diarylmethylpiperazines is described. The synthetic route enables preparation of a variety of enantiomerically pure amines with different N-alkyl groups. The invention includes an asymmetric addition of organometallic compounds to chiral sulfinimine to give adducts in predominantly one diastereomeric form. After purification by chromatography or crystallisation the pure diastereomer can subsequently be transferred into the corresponding pure enantiomers of by cleavage of the chiral auxilliary which is followed by synthesis of the piperazine ring by alkylation procedures.

The present invention thus relates to a novel asymmetric process for the preparation of compounds of the general formula (I)

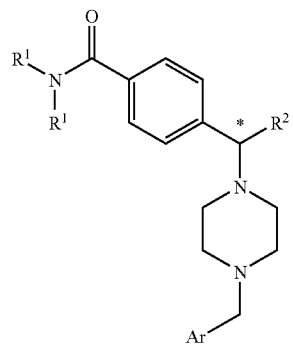

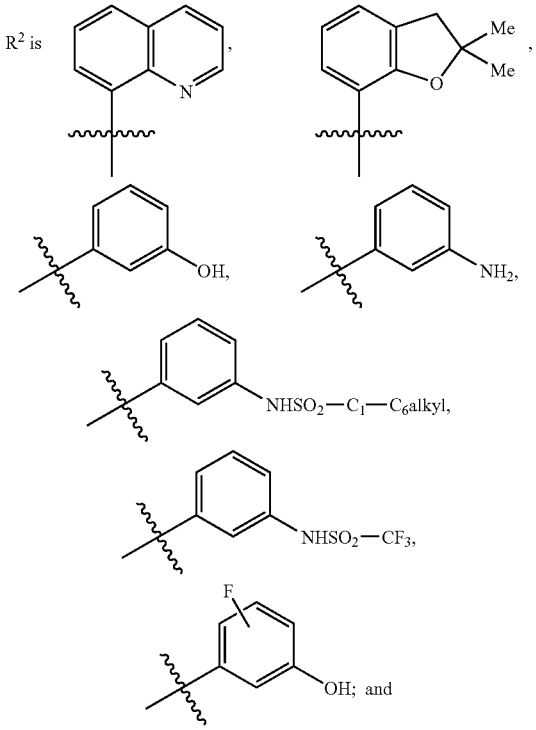

wherein
$R^1$ is $C_1$–$C_6$ alkyl, $R^2$ is

Ar is selected from any one of phenyl, pyridinyl, thienyl, furanyl, imidazolyl, or triazolyl.

As used herein, the term "$C_1$–$C_6$" alkyl denotes a straight or branched alkyl group having from 1 to 6 carbon atoms. Examples of said $C_1$–$C_6$ alkyl include, but is no limited to, methyl, ethyl, n-propyl, iso-propyl, n-butyl, iso-butyl, sec-butyl, t-butyl and straight- and branched-chain pentyl and hexyl.

The term "$C_1$–$C_6$ alkoxy" denotes a group O—$C_1$–$C_6$ alkyl, wherein $C_1$–$C_6$ alkyl is as defined above.

The term "halogen" includes fluoro, chloro, bromo and iodo.

The term "hydride donating reagent", is a compound that can deliver a hydride to an imine thereby giving the corresponding amine. Examples of such hydride donating reagent include, but is not limited to, sodium borohydride, sodium cyanoborohydride and sodium triacetoxyborohydride, The asymmetric center is denoted "*" in all figures. The present invention thus relates to enantiomerically pure compounds of FIG. 1, as either the isolated R-enantiomer or the corresponding isolated S-enantiomer. Isolated enantiomers prepared according to the present invention can also be shown by indicating the optical rotation of an exemplified compound, e.g. (+)-6.

In a preferred embodiment of the present invention, $R^1$ is ethyl or isopropyl, $R^2$ is

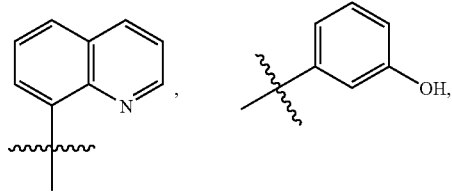

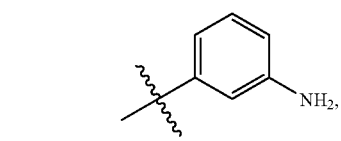

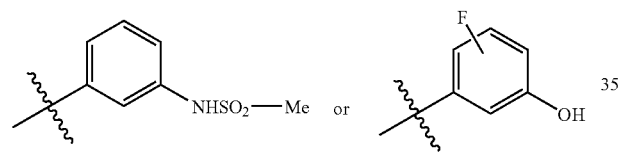

and Ar is phenyl, pyridyl, thienyl, or furanyl.

In a more preferred embodiment of the present invention, $R^1$ is ethyl or isopropyl, $R^2$ is

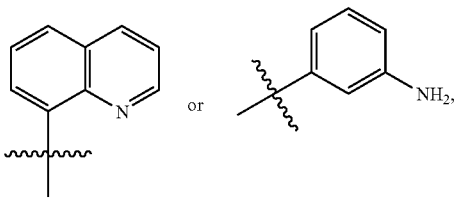

and Ar is phenyl or thienyl.

Each $R^2$ and Ar heteroaromatic ring may optionally and independently be further substituted by up to three additional substituents selected from $C_1$–$C_6$ alkyl, $NO_2$, $CF_3$, $C_1$–$C_6$ alkoxy, chloro, fluoro, bromo, and iodo. Preferred substituent is methyl. The substitutions on the heteroaromatic ring may be in any position on said ring systems.

Step 1

The novel asymmetric process of the present invention comprises the step of reacting a enantiomerically pure compound of the general formula (II)

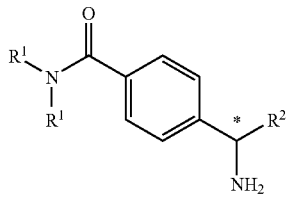

wherein $R^1$ and $R^2$ are as defined above, with N,N-bis(2-chloroethyl-2-nitrobenzeneamide of formula (III)

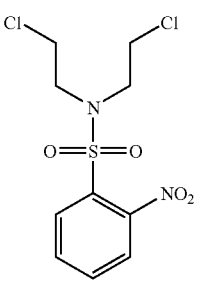

to give compounds of the general formula (IV)

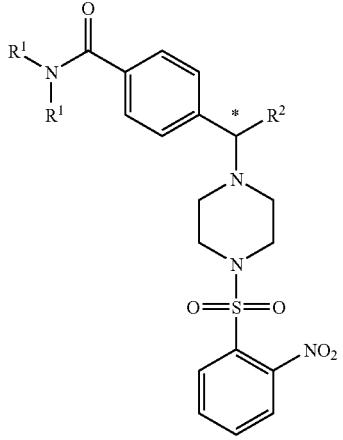

wherein $R^1$ and $R^2$ are as defined above. The reaction is carried out in an solvent at elevated temperature, such as reflux, in the presence of a base, such as a tertiary amine, for 10 to 50 hours. A molar excess of N,N-bis(2-chloroethyl)-2-nitrobenzenesulfonamide is used, e.g. 1.5 to 6, and is preferably added in portions to give a complete reaction.

Use of the 2-nitrobenzenesulfonate group is advantageous since It surprisingly can be cleaved off using conditions. These mild conditions are milder than the corresponding condition for other groups, such as the toluenesulfonate (tosylate) group. Mild deprotection conditions gives a cleaner reaction profile, less by-products, easier purification and increased yield. 2-nitrobenzenesulfonate group is thus the preferred N-protecting group to be used according to the present invention.

Step 2

The 2-nitrobenzenesulfonyl group of compounds of the general formula (IV) is thereafter cleaved by standard conditions, i.e. by using a sulfur nucleophile, such as thiophenol or mercaptoacetic acid, in the presence of a base, such as potassium carbonate, to give compounds of the general formula (V)

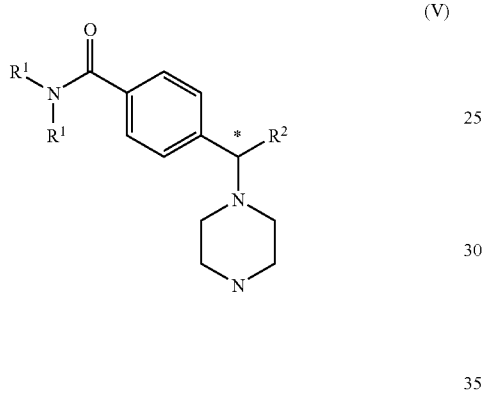

(V)

wherein $R^1$ and $R^2$ are as defined above

Step 3

Compounds of general formula (V) is thereafter alkylated under standard conditions using either;

i) a compound of the general formula Ar—CH$_2$—X, wherein Ar is as defined above and X is halogen, preferably bromide, and a suitable base, or ii) a compound of the general formula Ar—CHO, wherein Ar is as defined above, and a suitable reducing agent to give compounds of the general formula (I), as defined above.

Suitable bases to be used in the standard alkylation step i) above includes, but is not limited to, triethylamine and potassium carbonate.

Suitable reducing agents to be used in the standard reduction step ii) includes, but is not limited to, sodium cyanborohydride and sodium triacetoxyborohydride.

Non limiting examples of step 1 to 3 is shown below in Scheme 1.

The asymmetric key intermediate of the general formula (II) defined above is prepared by a process comprising the following steps.

Step 4

(1R,2S,5R)-(−)-Menthyl (S)-p-toluenesulfinate of the formula (VI)

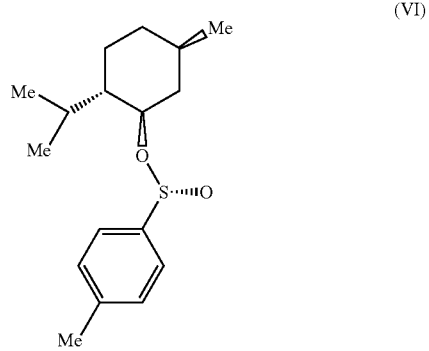

(VI)

is reacted with lithium hexamethyldisilazan and a compound of the general formula $R^2$—CHO, wherein $R^2$ is as defined above, to give a sulfimines of the general formula (VII)

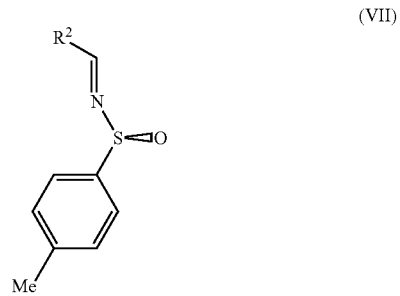

(VII)

wherein $R^2$ is as defined above. The reaction is carried out in an inert solvent, such THF, at around −78° C. under nitrogen atmosphere and for a few hours. A molar excess, such as 1.5 to 2 eq., of lithium hexamethyldisilazan is added first at the temperature is then increased to about room temperature for a few hours, e.g. 1–4 hours. The reaction is thereafter cooled again to around −78° C. and a molar excess of the aldehyde, e.g. 1 to 1.5 eq., is added and left for a few hours, e.g. 1 to 4 hours.

Step 5 p-Iodo-benzamide derivatives of the general formula (VIII)

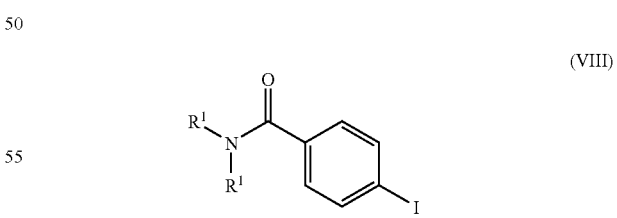

(VIII)

wherein $R^1$ is as defined above, is reacted with an alkyl lithium reagent, such as butyl lithium, in an inert solvent, such as THF, and low temperature, such as −78° C. and the sulfinimide prepared in step 4 above is added and allow to react for few minutes, such as 5 to 15 minutes, to give a diastereomeric mixture of the compounds of the general formula (IX)

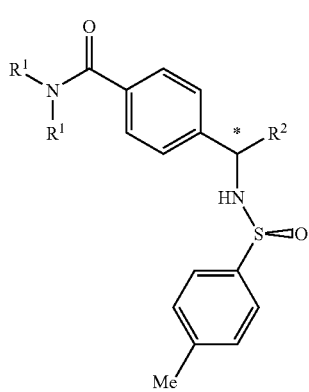

wherein R¹ and R² are as defined above.

The diastereomeric ratio of the products of step 5 is 70/30, preferably 80/20 and more preferably 90/10. The two diastereomers can thereafter be purified (from the other diastereomer) by standard techniques like crystallization or chromatography.

Step 6

The purified diastereomer of the general formula (IX), prepared in step 5 above, is thereafter solvolyzed, e.g. methanolysis, by brief acid treatment to give the intermediate compound of the general formula (II)

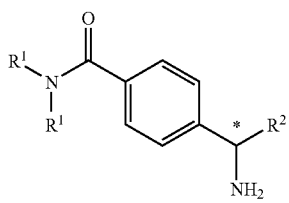

wherein R¹ and R² are as defined above.

The enantiomeric excess (ee) of compounds of the general formula (II) prepared according to steps 4 to 6 of the present invention is >90%, preferably >95% and more preferably >98%.

If (1R,2S,5R)-(+)-menthyl (R)-p-toluenesulfinate is used in step 4 above and subsequent steps 5 and 6 are performed as the described the other optical isomer (enantiomer) of the compound of the general formula (II) will be obtained.

Non-limiting examples of steps 4 to 6 are shown below in Scheme 1.

In another embodiment of the present invention, asymmetric key intermediate compounds of general formula (II) is prepared by a process comprising the following steps.

Step 7

An aldehyde of the structure R²—CHO, wherein R² are as defined above, is reacted with (R)-(+)-2-methyl-2-propanesulfinamide to give a compound of the general formula (X)

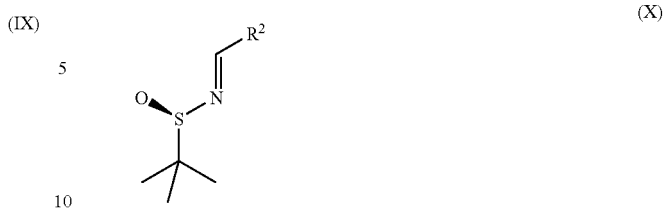

wherein R² is as defined above.

The reaction is carried out using excess titanium tetraethoxide, e.g. 1.1 to 2 eq., in a solvent, such as THF, at elevated temperature, such as 40–80° C., for a number of hours, such as 2–18 hours.

Step 8 p-Iodo-benzamide derivatives of the general formula (VIII)

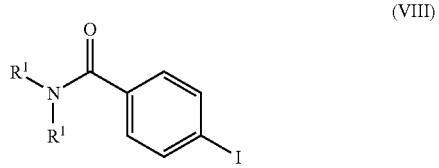

wherein R¹ is as defined above, is reacted with an alkyl lithium reagent, such as butyl lithium, in an Inert solvent, such as THF, and low temperature, such as −78° C. and the sulfinimide prepared in step 7 above is added and allow to react for few minutes, such as 5 to 15 minutes, to give a diastereomeric mixture of the compounds of the general formula (XI)

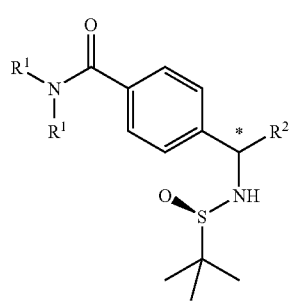

wherein R¹ and R² are as defined above.

The diastereomeric ratio of the products of step 8 is 70/30, preferably 80/20 and more preferably 90/10. The two diastereomers can thereafter be purified (from the other diastereomer) by standard techniques like crystallization or chromatography.

Step 9

The purified diastereomer of the general formula (XI), prepared in step 8 above, is thereafter solvolyzed, e.g. methanolysis, by brief acid treatment to give the intermediate compound of the general formula (II)

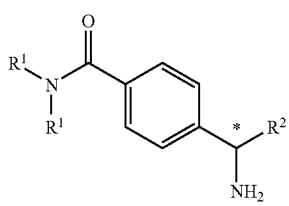

(II)

wherein R¹ and R² are as defined above.

The enantiomeric excess (ee) of compounds of the general formula (II) prepared according to step 7 to 9 of the present invention is >90%, preferably >95% and more preferably >98%.

If (R)-(−)-2-methyl-2-propanesulfinamide is used in step 7 above and subsequent steps 8 and 9 are performed as described the other optical isomer (enantiomer) of the compound of the general formula (II) will be obtained.

Non-limiting examples of steps 7 to 9 are shown below in Scheme 2.

In another embodiment of the present invention, asymmetric key intermediate compounds of general formula (II) is prepared by a process comprising the following steps.

Step 10

A ketone of the general formula (XII)

(XII)

wherein R¹ and R² are as defined above, is reacted with (R)-(+)-2-methyl-2-propanesulfinamide as described in step 7 above to give compounds of the general formula (XIII)

(XIII)

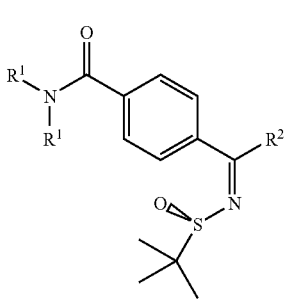

wherein R¹ and R² are as defined above.

Step 11

Compounds of the general formula (XIII) is thereafter reduced using a hydride donating reagent, such as sodium borohydride, under standard conditions, to give a diastereomeric mixture of the compounds of the general formula (XI)

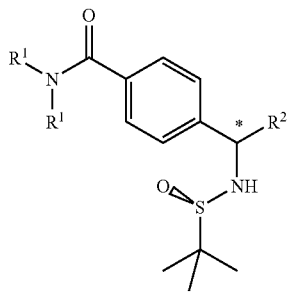

(XI)

wherein R¹ and R² are as defined above.

The diastereomeric ratio of the products of step 11 is 70/30, preferably 80/20 and more preferably 90/10. The two diastereomers can thereafter be purified (from the other diastereomer) by standard techniques like crystallization or chromatography.

Step 12

The purified diastereomer of the general formula (XI), prepared in step 11 above, is thereafter treated as described in step 9 above to give key intermediate compound of general formula (II)

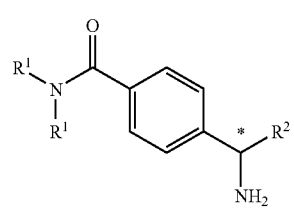

(II)

wherein R¹ and R² are as defined above.

The enantiomeric excess (ee) of compounds of the general formula (II) prepared according to step 10 to 12 of the present invention is >90%, preferably >95% and more preferably >98%.

If (R)-(−)-2-methyl-2-propanesulfinamide is used in step 10 above and subsequent steps 11 and 12 are performed as described the other optical isomer (enantiomer) of the compound of the general formula (II) will be obtained.

Non-limiting examples of steps 10 to 12 are shown below in Scheme 3.

Step 13

Ketone of the general formula (XII) above is prepared by treating a compound of general formula (VIII) above with an alkyl lithium reagent, such as butyl lithium, in an inert solvent, such as THF, and low temperature, such as −78° C. and thereafter adding a compound of the general formula R²—CHO, wherein R² is as defined above, and allow it to react for few minutes, such as 5 to 15 minutes to give a compound of general formula (XIV)

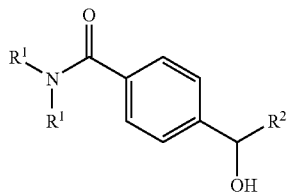
(XIV)

wherein $R^1$ and $R^2$ are as defined above, which is thereafter oxidized under standard conditions, e.g: using pyridinium dichromate, to the corresponding ketone of the general formula (XII), as defined above.

It will be appreciated by those skilled in the art that in the process described above the functional groups of starting materials or intermediate compounds may need to be protected by protecting groups.

Functional groups which it is desirable to protect include hydroxy and amino groups. Protecting groups may be added and removed in accordance with techniques which are well known to those skilled in the art. The use of protecting groups is described in 'Protective Groups in Organic Synthesis', 2nd edition, T. W. Greene & P. G. M. Wutz, Wiley-Interscience (1991). The protective group may also be a polymer resin such as Wang resin or a 2-chlorotrityl chloride resin.

The present invention is thus more practical, easier to perform under controlled conditions, less sensitive to reaction conditions, more general, gives a higher yield than any other asymmetric process for making diarylmethylpiperazines and diarylmethylamines.

Intermediates

Another object of the present invention is to provide new intermediate compounds for use in the described process.

Thus, one aspect of the present invention is a compound of the general formula (II)

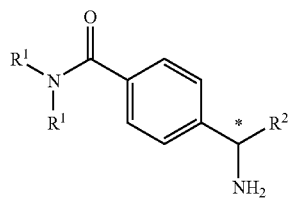
(II)

wherein
$R^1$ is $C_1$–$C_6$ alkyl, and
$R^2$ is

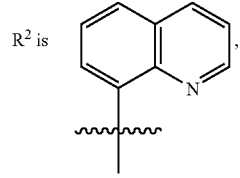

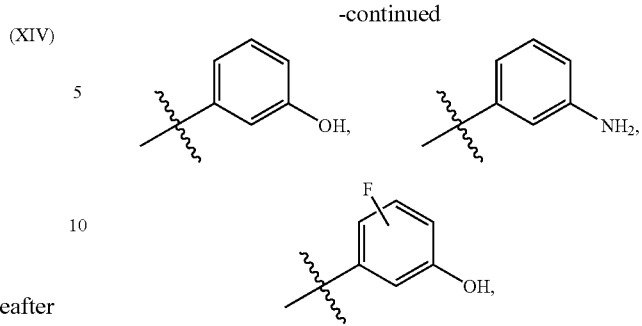

as a useful intermediate in the described process.

A preferred intermediate compound of the present invention is a compound of the general formula (II) wherein $R^1$ is methyl or isopropyl, and $R^2$ is

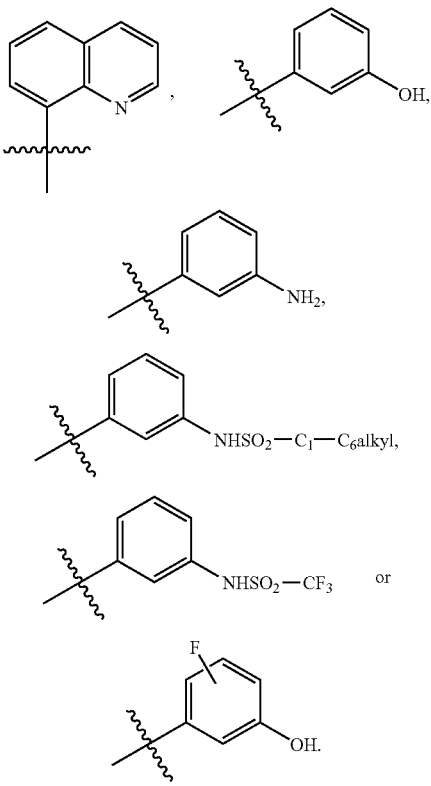

A more preferred intermediate compound of the present invention is a compound of the general formula (II) wherein $R^1$ is methyl or isopropyl, and $R^2$ is

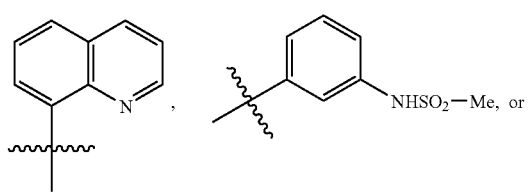

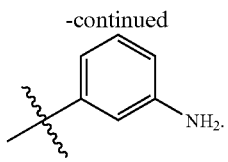

Each R² ring may optionally and independently be further substituted by up to three additional substituents selected from $C_1$–$C_6$ alkyl, $NO_2$, $CF_3$, $C_1$–$C_6$ alkoxy, chloro, fluoro, bromo, and iodo: The substitutions may be in any position on said ring systems;

Novel Compounds

The following novel compounds have been prepared by the present invention.

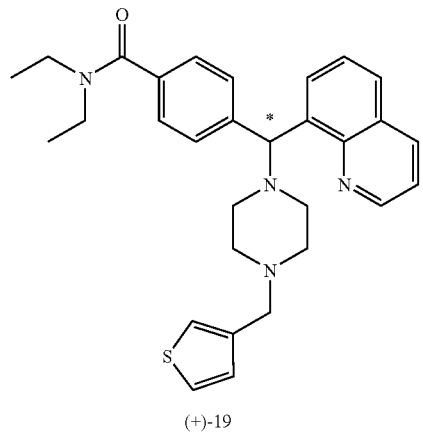

(+)-19

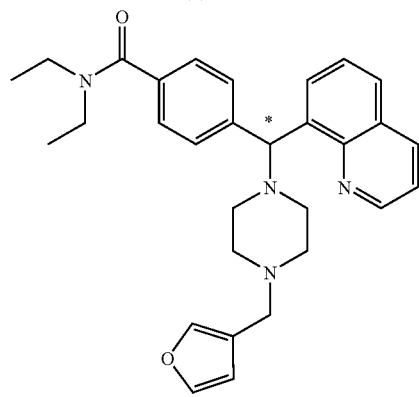

(+)-20

The invention is illustrated, but in no way limited, by the following examples.

EXAMPLES

Step 1

(−)-N,N-diethyl-4-[{4-[(2-nitrophenyl)sulfonyl]-1-piperazinyl}(8quinolinyl)methyl]-benzamide (8).

(−)-6 (0.14 g, 0.42 mmol) was dissolved in toluene (2 mL) with Et3N (1 mL). N,N-bis(2-chloroethyl)-2-nitrobenzenesulfonamide (0.20 g, 0.61 mmol) was added and the reaction stirred at 110° C. Two more additions of N,N-bis(2-chloroethyl)-2-nitrobenzenesulfonamide were made during 36 h before the reaction was complete. Purification by chromatography on silica gave (−)-8 (90 mg, 36%). 1H NMR (CDCl3): δ 1.2, 1.1 (m, 6H), 2.60 (m, 4H), 3.1–3.6 (m, 8H), 6.10 (s, 1H), 7.20–8.15 (m, 13H), 8.92 (m, 1H ).

Step 2

(−)-N,N-diethyl-4-[1-piperazinyl(8-quinolinyl)methyl]benzamide (9).

(−)-8 (90 mg, 0.15 mmol) was dissolved in DMF (6 mL) and $K_2CO_3$ (0.25 g, 1.8 mmol) and thiophenol (66 µL, 0.6 mmol) was added. Stirring was continued for 2 h at 25° C. Purification by reverse phase chromatograpy (LiChroprep RP-18). Extraction ($CH_2Cl_2$/$K_2CO_3$ (aq)) and evaporation gave (−)-9 (40 mg, 66%). IR (KBr, $v_{max}$) 3297, 2982, 2716, 2474, 1611, 1434, 1380, 1288, 1098 $cm^{-1}$. MS (amine): 402, 318, 246, 217, 109. $^1$H NMR (amine, CDCl3): δ 1.2, 1.1 (2s, 6H), 2.94, 2.51 (2m, 8H), 3.5–3.1 (m, 5H), 6.05 (s, 1H), 8.94–7.20 (m, 10H).

Step 3

(+)-4-[(4-benzyl-1-piperazinyl)(8-qulnolinyl)methyl]-N,N-diethylbenzamide (10).

A sample of (+)-9 (0.40 g, 1.0 mmol) and triethylamine (0.28 mL, 2.0 mmol) was dissolved in MeCN (5 mL). Benzyl bromide (0.24 mL, 2.0 mmol) was added with stirring at 25° C. After 12 h the solution was concentrated and purified by reverse phase chromatograpy (LiChroprep RP-18). After extraction ($CH_2Cl_2$/$K_2CO_3$(aq)) the free base was obtained (+)-10 (0.47 g, 95%) IR (2×HCl, KBr): 2388, 1606, 1434, 1356, 1287 (cm−1). $^1$H NMR (free amine, CDCl3) δ=1.05 (m, 6H), 2.5 (m, 8H), 3.1–3.6 (m, 6H), 6.04 (s, 1H), 7.18–8.98(m, 15H). Anal. ($C_{32}H_{38}Cl_2N_4O$) C, H, N.

Step 4

(+)-(S)-4-methyl-N-[(E)-8-quinolinylmethylidene]benzenesulfinamide (3).

(1R,2S,5R)-(−)-Menthyl (S)-p-toluenesulfinate (6.0 g, 20 mmol) was disolved in THF (100 mL) and cooled to −78° C. under nitrogen. Lithium hexamethyldisilazan (1.0 M, 26 mL, 26 mmol) was added dropwise and solution was stirred at 25° C. for 2 h. The solution was cooled again to −78° C. and 8-quinolylaldehyde (3.5 g, 22 mmol) was added dissolved in THF (2 mL). After stirring 2 h at −78° C., water was added and the mixture was extracted with ether/water. The organic phase was dried ($MgSO_4$), evaporated in vacuo, and the residue purified by chromatography on silica to give 3 (4.1 g, 67%). $^1$H NMR (CDCl3): δ 2.40 (s, 3H), 7.32 (m, 2H), 7.48 (m, 1H), 7.61 (m, 1H), 7.71 (m, 2H), 7.99 (m, 1H), 8.19 (m, 1H), 8.45 (m, 1H), 9.01 (m, 1H), 10.27 (s, 1H).

Step 5

(+)-N,N-diethyl-4-[{[(S)-(4-methylphenyl)sulfinyl]amino}(8-quinolinyl)methyl]-benzamide (5).

N,N-diethyl 4-iodo-benzamide (3.1 g, 10 mmol) was dissolved in dry toluene/THF (9:1, 200 mL) and cooled to −78° C. under nitrogen. n-BuLi (7.8 mL, 1.3 M in hexane, 10 mmol) was added dropwise during 5 to 10 min. After further 5 min, 3 (1.0 g, 3.4 mmol) was added dissolved in toluene. (1 mL). The solution was stirred 10 min, then $NH_4Cl$ (aq.) was added. Concentration, aqueous workup and chromatography on silica gave a total of 0.70 g (44%) of a 70:30 mixture of diastereomers. The pure major isomer 5 (0.37 g) was obtained by one more chromatography. $^1$H NMR (CDCl3): δ 1.2 (m, 6H), 2.4 (s, 3H), 3.4 (m, 4H), 6.35 (d, J=7.5 Hz, 1H), 6.61 (d, J=7.5 Hz, 1H), 7.15–7.55 (m, 11H), 7.75(m, 1H), 8.12 (m, 1H ), 8.75 (m, 1H).

Step 6

(−)-4-[amino(8-quinolinyl)methyl]-N,N-diethylbenzamide [(−)-6].

Treatment of 5 (0.37 g, 0.79 mmol) with trifluoroacetic acid (123 μL, 1.6 mmol) in MeOH (5 mL) at 25° C., for 12 h. Concentration in vacuo and reverse phase chromatography gave 6 (0.15 g, 53%). $^1$H NMR (CDCl$_3$): δ 1.2 (m, 6H), 2.2 (s, 2H), 3.4 (m, 4H), 6.40 (s, 1H), 7.30–7.58(m, 7H), 7.71 (m, 1H), 8.15 (m, 1H), 8.92 (m, 1H).

Step 7

(R-(+)-2-methyl-N-[(E)-8-quinotinylmethylidene]-2-propanesulfinamide (14).

(R)-(+)-2-methyl-2-propanesulfinamide (0.14 g, 1.2 mmol) and 8-quinolylaldehyde (0.19 g, 1.2 mmol) was dissolved in THF (5 mL) and titanium tetraetoxide (1 mL, ~2.4 mmol) was added. The solution was heated at 65° C. for 12 h, then concentrated in vacuo. Purification by chromatography on silica to give 14 (0.29 g, 93%). $^1$H NMR (CDCl$_3$): δ 1.31 (s, 9H), 7.49 (m, 1H), 7.66 (m, 1H), 8.01 (m, 1H), 8.21 (m, 1H), 8.49 (m, 1H), 9.02 (m, 1H), 10.09 (s, 1H).

Step 8

4-[[(tert-butylsulfinyl)imino](8-quinolinyl)methyl]-N,N-diethylbenzamide (15).

N,N-diethyl 4-iodo-benzamide (0.18 g, 0.6 mmol) was dissolved in dry THF (4 mL) and cooled to −78° C. under nitrogen. n-BuLi (0.46 mL, 1.3 M in hexane, 0.6 mmol) was added dropwise during 5 to 10 min. After further 5 min, the solution was added with canual to 14 (78 mg, 0.30 mmol) dissolved in THF (2 mL) and cooled to −78° C. The solution was stirred 10 min, then NH$_4$Cl (aq.) was added. Concentration, aqueous workup and chromatography on silica gave a product (135 mg) containing 15 as a 80:20 mixture of diastereomers and some unreacted N,N-diethyl 4-iodo-benzamide.

Step 9

(+)-4-[amino(8-quinolinyl)methyl]-N,N-diethylbenzamide ((+)-6).

Treatment of 15 (135 mg, ~0.30 mmol) with HCl in ether (0.3 mL, 0.6 mmol) in MeOH (2 mL) at 25° C., for 5 min. Concentration in vacuo, dilution with water, washing with EtOAc. The solution was then made basic with K$_2$CO$_3$(aq), extracted with and evaporated to give (+)-6 (53 mg, 53% from 14). $^1$H NMR (CDCl$_3$): δ 1.2 (m, 6H), 2.2 (s, 2H), 3.4 (m, 4H), 6.40 (s, 1H), 7.30–7.58 (m, 7H), 7.71 (m, 1H), 8.15 (m, 1H), 8.92 (m, 1H).

Treatment of (+)-6 with (R)-(−)-α-methoxy-α-(trifluoromethyl)phenylacetyl chloride gave the diastereomeric derivative. $^1$H NMR (major diastereomer) (CDCl$_3$): δ 1.0–1.2 (2m, 6H), 3.1, 3.5 (2m, 4H), 3.43 (s, 3H), 6.82 (d, J=9.0, 1H), 7.10–7.40 (m, 9H), 7.52 (m, 1H), 7.71 (m, 1H), 7.79 (m, 1H), 8.14 (m, 1H), 8.68 (m, 1H), 9.83 (d, J=9.0, 1H).

Step 10

(−)-(4[[(tert-butylsulfinyl)imino](8-quinolinyl )methyl]-N,N-diethylbenzamide (18).

13 (0.25 g, 2.0 mmol) and 17 (0.66 g, 2.0 mmol) was dissolved in THF (20 mL) and titanium tetraetoxide (2.5 mL, 4 mmol) was added. The solution was heated at 65° C. for 3 days, then concentrated in vacuo. Purification by chromatography on silica to give 18 (0.44 g, 50%). $[α]_D^{20}$=−144° (c 132, CH$_2$Cl$_2$). $^1$NMR (CDCl$_3$): δ 1.10, 1.25 (2m, 6H), 1.31 (s, 9H), 3.20, 3.55 (2m, 4H), 7.30–7.80 (m, 7H), 7.97 (m, 1H), 8.24 (m, 1H), 8.86 (m, 1H), Step 11

4[[((tert-butysulfinyl)imino](8-quinolinyl)methyl]-N,N-diethylbenzamide (15).

18 (25 mg, 0.06 mmol) was dissolved in dry THF (1 mL) together with titanium tetraethoxide (18 μL, 0.12 mmol) and added to a suspension of sodium borohydride (9 mg, 0.23 mmol) in THF (1 mL) at −50° C. under nitrogen. The temperature was slowly raised to 0° C., 4 h and then the solution was worked up by addition of NH$_4$Cl (aq.). Concentration gave a crude product which was purified by chromatography on silica to give 15 (10 mg, 40%) as a mixture of diastereomers. $^1$H NMR (major diastereomer) (CDCl$_3$): δ 1.0–1.2 (2m, 6H), 1.23 (s, 9H), 3.1, 3.5 (2m, 4H), 6.30 (m, 1H), 7.20–7.50 (m, 9H), 7.58 (m, 1H), 7.60 (m, 1H), 8.10 (m, 1H), 8.79 (m, 1H).

Step 12

(−)-4-[amino(8-quinolinyl)methyl]-N,N-diethylbenzamide [(−)-6].

Treatment of 15 with HCl in MeOH for 10 min and extractive workup gave (−)-6. NMR data identical to 6 made previously. Treatment of (−)-6 with (R)-(−)-α-methoxy-α-(trifluoromethyl)phenylacetyl chloride gave the diastereomeric derivative in a 9:1 ratio as determined by NMR. $^1$H NMR (major diastereomer) (CDCl$_3$): δ 1.0–1.2 (2m, 6H), 3.1, 3.5 (2m, 4H), 3.42 (s, 3H), 6.82 (d, J=9.0, 1H), 7.10–7.50 (m, 9H), 7.55 (m, 1H), 7.64 (m, 1H), 7.79 (m, 1H), 8.19 (m, 1H), 8.78 (m, 1H), 9.90 (d, J=9.0, 1H).

Step 13

N,N-diethyl-4-(8-quinolinecarbonyl)benzamide (17).

N,N-diethyl4-iodobenzamide (4) (0.67 g, 2.2 mmol) was dissolved in dry THF (25 mL) and cooled to −78° C. under nitrogen. n-BuLi (1.3 mL, 1.6 M in hexane, 2.2 mmol) was added dropwise during 5 min. After further 10 min, 8-formylquinoline (0.17 g, 1.1 mmol) was added dissolved in THF (1 mL). The solution was stirred 1 h, then NH4Cl (aq.) was added. After concentration, aqueous workup and chromatography on silica a total of 0.29 g (78%) N,N-diethyl-4-[hydroxy(8-quinolinyl)methyl]benzamide (16). was obtained. MS: 334, 262, 234, 215, 204, 178, 156, 129.

16 (3.0 g, 9.0 mmol) was dissolved in CH$_2$Cl$_2$ (25 mL) and powdered pyridinium dichromate (PDC) (5.0 g, 13 mmol) was added portionwise at 25° C. Two more portions of PDC (0.5 g) were added after 3 h and 12 h. After 24 h, the solution was diluted with heptane and filtered through silica gel. Elution with EtOAc and evaporation in vacuo gave 17 (1.8 g, 60%). MS: 332, 303, 275, 260, 232, 204, 176, 156, 128, 115. $^1$H NMR (CDCl$_3$): δ 1.1, 1.3 (2m, 6H), 3.22, 3.55 (2m, 4H), 7.39 (d, J=8 Hz, 2H), 7.43 (m, 1H), 7.65 (m, 1H), 7.75 (m, 1H), 7.86 (d, J=8 Hz, 2H), 7.98 (m, 1H), 8.23 (m, 1H), 8.83 (m, 2H).

(+)-N,N-diethyl-4-{8-quinolinyl[4-(3-thienylmethyl)-1-piperazinyl]methyl}benzamide ((+)-19)

Compound (+)-9 (0.60 mg, 1.5 mmol) and 3-thiophenecarboxaldehyde (0.28 mL, 3.0 mmol) was dissolved in MeOH (5 mL) and AcOH was added (43 μL, 0.75 mmol). After stirring 1 h, NaBH$_3$CN (94 mg, 1.5 mmol) was added in portions over 6 h. After stirring over night, the solution was concentrated and the product purified by reverse phase chromatography (LiChroprep RP-18, 10–80% MeCN in water, 0.1% TFA) to give (+)-19 as the bis-trifluoroacetate (0.57 g, 77%). $[α]_D^{20}$=+84.5° (c 0.87, MeOH). $^1$H NMR (CD$_3$OD) δ=1.1, 1.2 (2m, 6H), 3.2–3.5 (m, 12H), 4.35 (s, 2H), 6.19 (s 1H), 7.20 (m, 1H), 7.28 (d, J=8 Hz, 2H), 7.50 (m, 1H), 7.55 (m, 1H), 7.58–7.66 (m, 2H), 7.70 (d, J=8 Hz, 2H), 7.83 (m, 1H ), 8.07 (m, 1H ), 8.28 (m, 1H), 8.94 (m, 1H).
(+)-N,N-diethyl-4-[[4-(3-furylmethyl)-1-piperazinyl](8-quinolinyl)methyl]benzamide ((+)-20).
Procedure as (+)-19. Reaction of (+)-9 (50 mg, 0.12 mmol) with 3-furancarboxaldehyde (21 μL, 0.24 mmol) gave (+)-20 as the bis-trifluoroacetate (58 mg, 68%). $[α]_D^{20}$=+78.2° (c 0.60, MeOH). $^1$ NMR (CD$_3$OD) δ=1.1, 1.2 (2m, 6H), 3.1–3.6 (m, 12H), 4.21 (s, 2H), 6.19 (s, 1H), 6.58 (s, 1H), 7.28 (d, J=8 Hz, 2H), 7.50 (m, 1H), 7.61 (m, 2H), 7.70 (d, J=8 Hz, 2H), 7.74 (s, 1H), 7.83 (m, 1H), 8.07 (m, 1H), 8.28 (m, 1H), 8.94 (m, 1H).
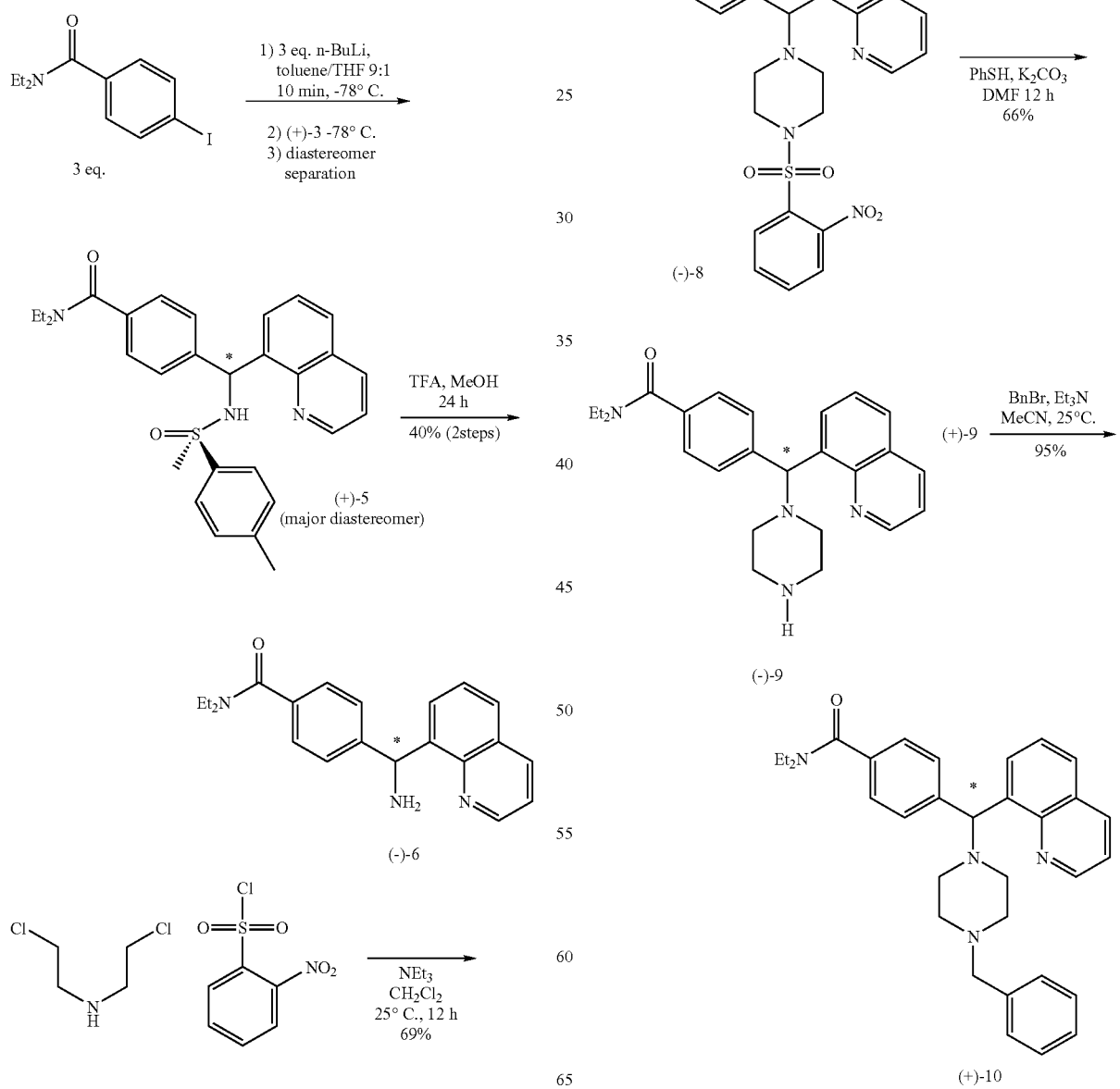
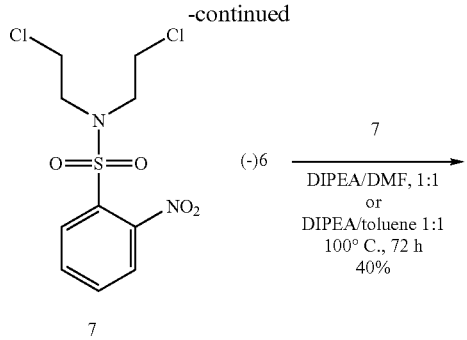
Scheme 1.

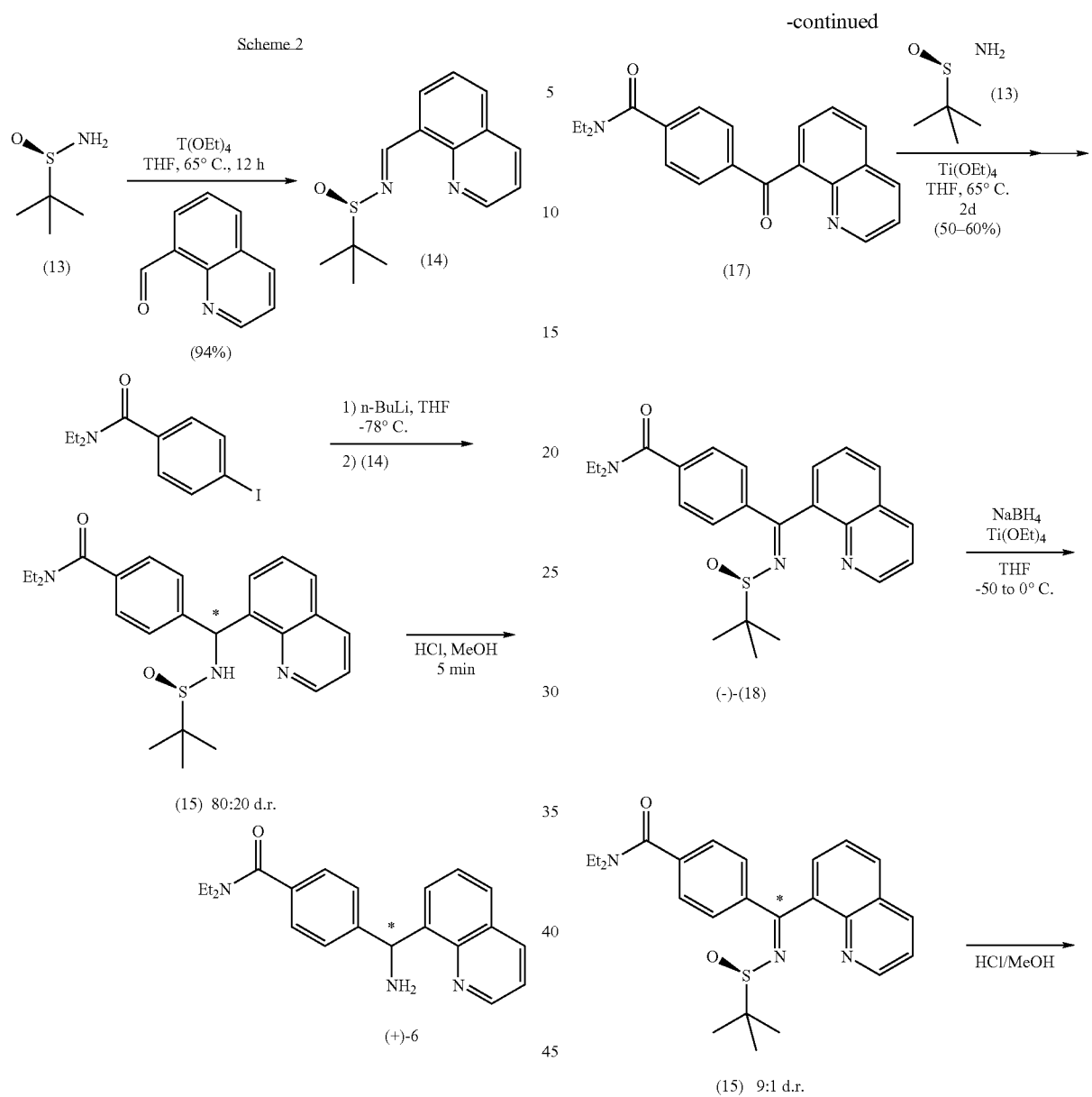
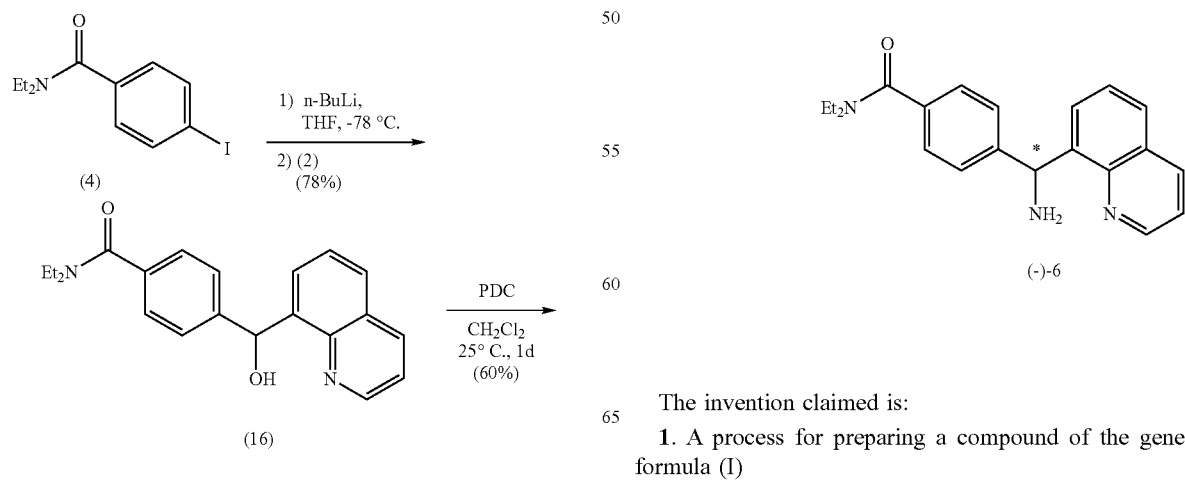
The invention claimed is:
1. A process for preparing a compound of the general formula (I)

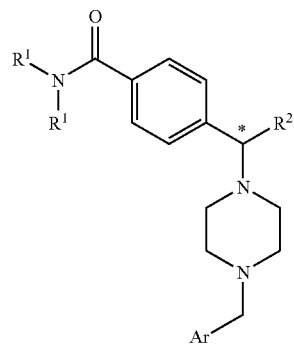

wherein

R¹ is $C_1$–$C_6$ alkyl,

R² is

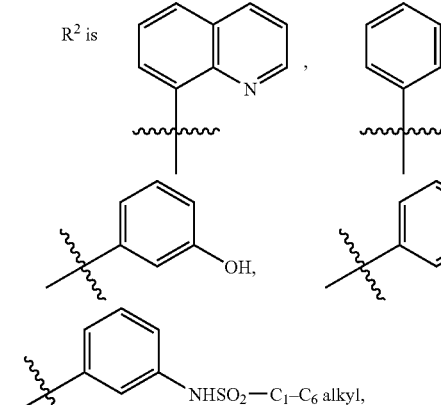

Ar is selected from any one of phenyl, pyridinyl, thienyl, furanyl, imidazolyl, or triazolyl, comprising the steps of;

A) reacting a enantiomerically pure compound of the general formula (II)

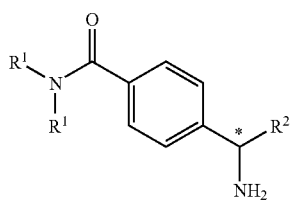

wherein R¹ and R² are as defined above, with N,N-bis (2-chloroethyl)-2-nitrobenzeneamide of formula (III)

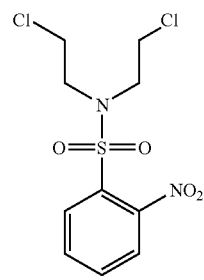

to give compounds of the general formula (IV)

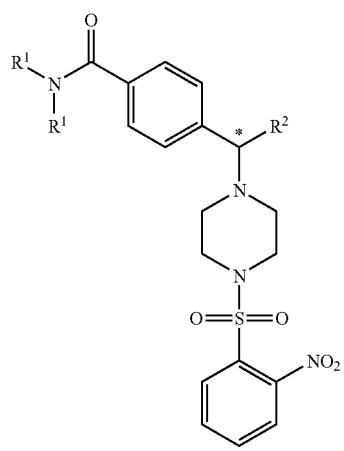

wherein R¹ and R² are as defined above,

B) Cleaving the 2-nitrobenzenesulfonyl group of compounds of the general formula (IV) to give compounds of the general formula (V)

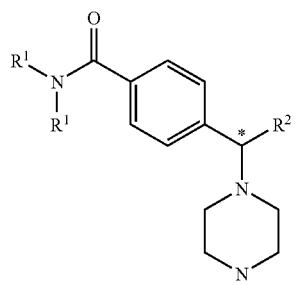

wherein R¹ and R² are as defined above, and

C) Alkylating a compound of general formula (V);

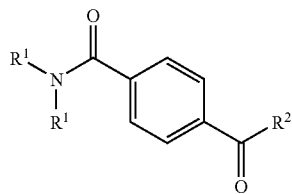

(XII)

wherein R¹ and R² are as defined in claim 1, with (R)-(+)-2-methyl-2-propanesulfinamide or (S)-(−)-2-methyl-2-propanesulfinamide to give a compound of the general formula (XIII)

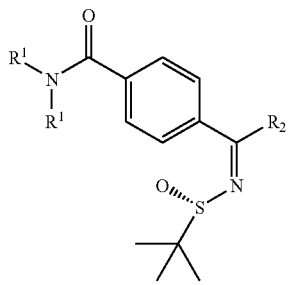

(XIII)

or its enantiomer, wherein R¹ and R² are as defined in claim 1,

B) reducing a compound of the general formula (XIII) using a hydride donating reagent, to give a compound of the general formula (XI)

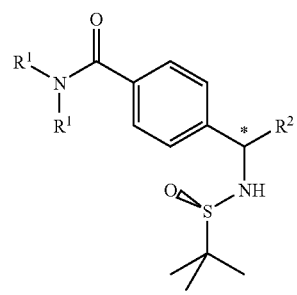

(XI)

wherein R¹ and R² are as defined in claim 1,

C)) methanolysing by acid treatment a compound of the general formula (XI) to give a compound of the general formula (II)

i) a compound of the general formula Ar—CH$_2$—X, wherein Ar is as defined above and X is halogen, and a suitable base, or ii) a compound of the general formula Ar—CHO, wherein Ar is as defined above, and a suitable reducing agent to give compounds of the general formula (I), as defined above.

2. A process according to claim 1, wherein R¹ is methyl or isopropyl, R² is

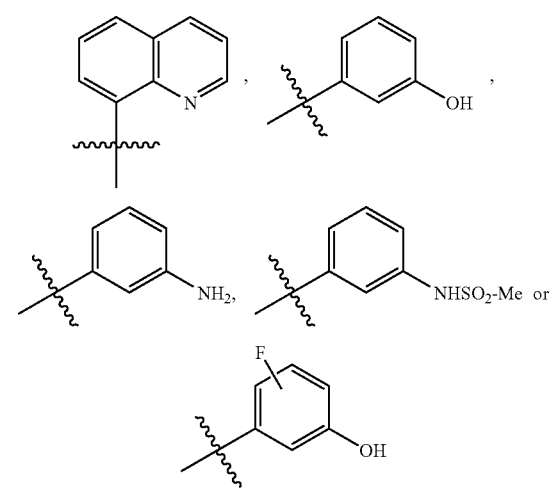

and Ar is phenyl, pyridyl, thienyl, or furanyl.

3. A process according to claim 1, wherein R¹ is methyl or isopropyl, R² is

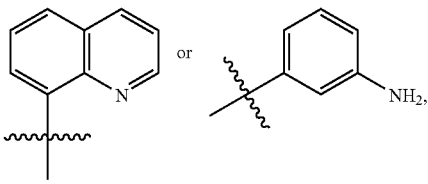

and Ar is phenyl or thienyl.

4. A process according to claim 1, wherein a compound of the general formula (II) is prepared by A) reacting (1R,2S,5R)-(−)-menthyl (S)-p-toluenesulfinate or (1R,2S,5R)-(+)-menthyl (R)-p-toluenesulfinate with lithium hexamethyldisilazan and a compound of the general formula R²—CHO, wherein R² is as defined in claim 1, to give a sulfimine of the general formula (VII)

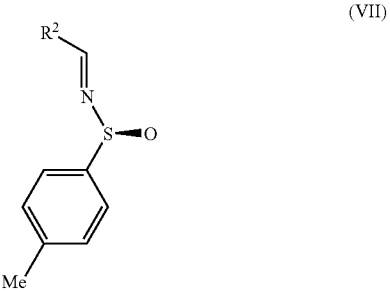

(VII)

or its enantiomer, wherein R² is as defined in claim 1,

B) reacting a p-Iodo-benzamide derivative of the general formula (VIII)

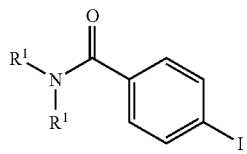

(VIII)

wherein R₁ is as defined in claim 1, with an alkyl lithium reagent and a sulfinimide prepared in step A above is thereafter added to give a compound, of the general formula (IX)

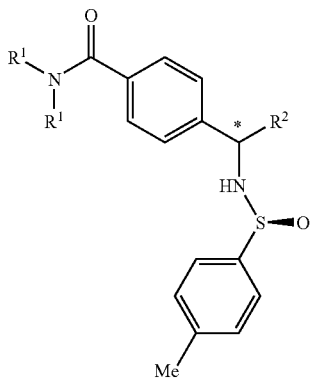

(IX)

wherein $R^1$ and $R^2$ are as defined in claim 1,

C) methanolysing by acid treatment of a compound of the general formula (IX) to give a compound of the general formula (II)

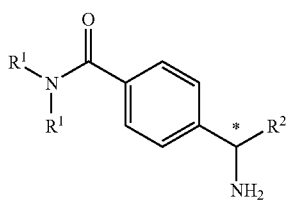

(II)

wherein $R^1$ and $R^2$ as defined in claim 1.

5. A process according to claim 1, wherein a compound of the general formula (II) is prepared by, A) reacting an aldehyde of the structure $R^2$—CHO, wherein $R^2$ are as defined in claim 1, with (R)-(+)-2-methyl-2-propanesulfinamide or (S)-(−)-2-methyl-2-propanesulfinamide to give a compound of the general formula (X)

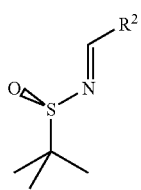

(X)

or its enantiomer, wherein $R^2$ are as defined in claim 1,

B) reacting a p-iodo-benzamide derivative of the general formula (VIII)

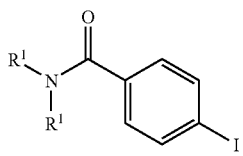

(VIII)

wherein R₁ is as defined in claim 1, with an alkyl lithium reagent and thereafter a sulfinimide prepared in step A above is added to give a compound of the general formula (XI)

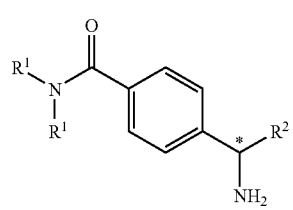

(XI)

wherein $R^1$ and $R^2$ are as defined in claim 1,

C) methanolysing by acid treatment a compound of the general formula (XI) to give a compound of the general formula (II)

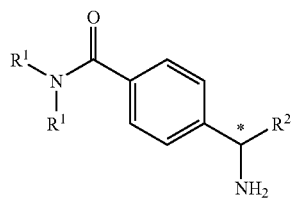

(II)

wherein $R^1$ and $R^2$ are as defined in claim 1.

6. A process according to claim 1, wherein a compound of the general formula (II) is prepared by, A) reacting a ketone of the general formula (XII)

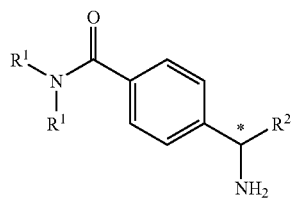

(II)

wherein $R^1$ and $R^2$ are as defined in claim 1.

* * * * *